(12) United States Patent
Varma

(10) Patent No.: US 12,220,152 B2
(45) Date of Patent: Feb. 11, 2025

(54) BALLOON FOR CERVICAL RIPENING

(71) Applicant: Obsolve Ltd, Brentwood (GB)

(72) Inventor: Rajiv Varma, Brentwood (GB)

(73) Assignee: Obsolve Ltd, Brentwood (GB)

( * ) Notice: Subject to any disclaimer, the term of this patent is extended or adjusted under 35 U.S.C. 154(b) by 0 days.

(21) Appl. No.: 18/150,077

(22) Filed: Jan. 4, 2023

(65) Prior Publication Data

US 2024/0216016 A1    Jul. 4, 2024

(51) Int. Cl.
*A61B 17/42* (2006.01)
*A61B 1/06* (2006.01)
*A61M 25/10* (2013.01)
*A61B 17/00* (2006.01)

(52) U.S. Cl.
CPC ............... *A61B 17/42* (2013.01); *A61B 1/06* (2013.01); *A61M 25/1011* (2013.01); *A61M 25/10185* (2013.11); *A61B 2017/00557* (2013.01); *A61B 2017/4225* (2013.01); *A61M 2210/1433* (2013.01)

(58) Field of Classification Search
CPC . A61B 17/42; A61B 1/06; A61B 2017/00557; A61M 25/1011; A61M 25/10185; A61M 2210/1433; A61M 29/02
See application file for complete search history.

(56) References Cited

U.S. PATENT DOCUMENTS

| | | | |
|---|---|---|---|
| 1,959,127 A * | 5/1934 | Duerme ................. | A61B 90/30 600/245 |
| 3,045,677 A * | 7/1962 | Wallace ............. | A61M 25/1011 606/192 |
| 4,976,692 A * | 12/1990 | Atad ................... | A61M 25/1011 604/101.03 |
| 5,947,991 A | 9/1999 | Cowan | |
| 6,066,090 A * | 5/2000 | Yoon .................. | A61B 17/3417 600/113 |
| 2002/0013601 A1 * | 1/2002 | Nobles ................. | A61M 29/02 606/193 |
| 2004/0116955 A1 * | 6/2004 | Foltz ..................... | A61M 31/00 606/193 |
| 2005/0055043 A1 | 3/2005 | Foltz et al. | |
| 2006/0058831 A1 * | 3/2006 | Atad ................ | A61M 25/1002 606/193 |
| 2009/0192542 A1 | 7/2009 | Harter | |

(Continued)

FOREIGN PATENT DOCUMENTS

| | | |
|---|---|---|
| CN | 110840536 A | 2/2020 |
| CN | 111973868 A * | 11/2020 |
| WO | WO-2005094257 A2 * | 10/2005 ............ A61F 5/003 |

*Primary Examiner* — Brigid K Byrd
(74) *Attorney, Agent, or Firm* — Levine Bagade Han LLP

(57) ABSTRACT

An intravaginal device for cervical ripening comprising an inflatable portion and a tube in fluid communication with the inflatable portion. The inflatable portion is configurable between a deflated and an inflated state, and the inflatable portion is configured to be inserted into a vagina when in the deflated state and to ripen a cervix when inflated with fluid. The tube is configurable between an extended state and a retracted state. In the extended state, the tube is configured to be located at least in part outside the vagina to deliver fluid to inflate the inflatable portion. In the retracted state, the tube is configured to be located within the vagina.

17 Claims, 5 Drawing Sheets

(56) References Cited

U.S. PATENT DOCUMENTS

2012/0143006 A1\* 6/2012 Avitsian ............ A61B 1/00144
                                                          600/121
2016/0310707 A1\* 10/2016 Ghodsian ............... A61B 17/42
2017/0014605 A1    1/2017 Schultz
2020/0383703 A1   12/2020 Atad et al.
2021/0128894 A1\*  5/2021 Burnette ............... A61M 29/02

\* cited by examiner

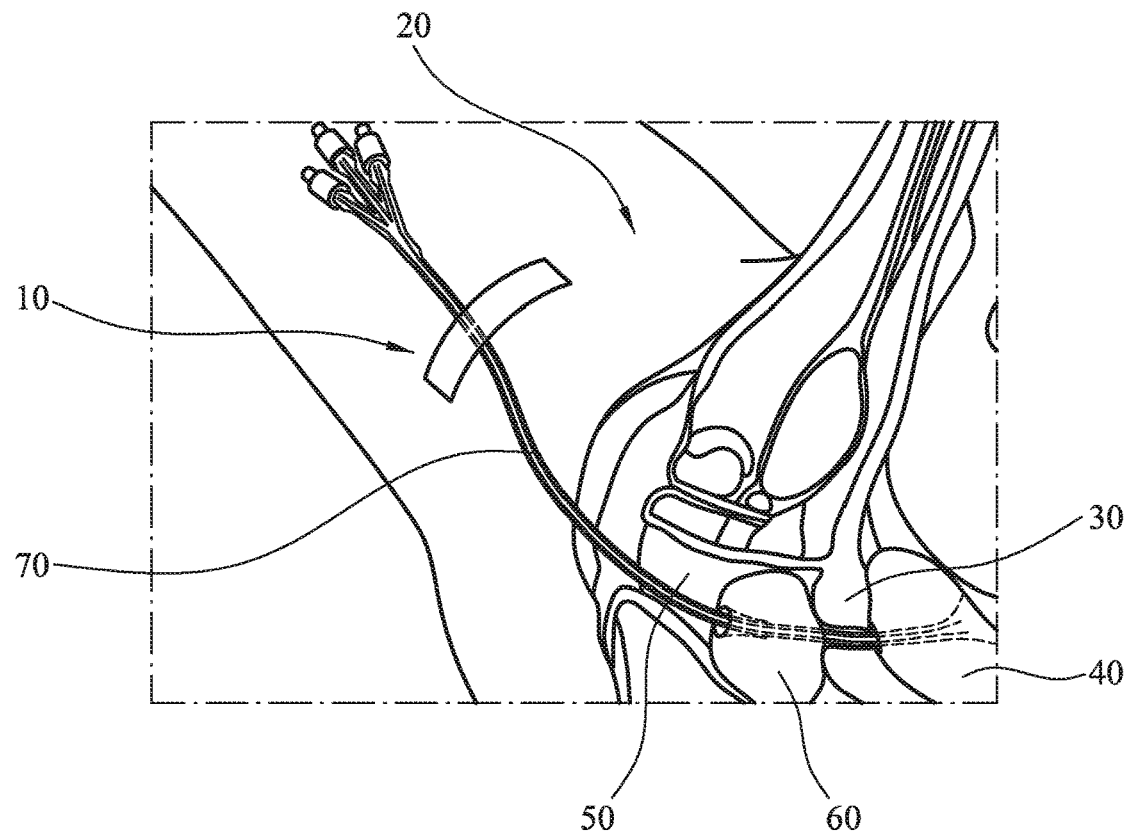
Figure 1 - Prior Art
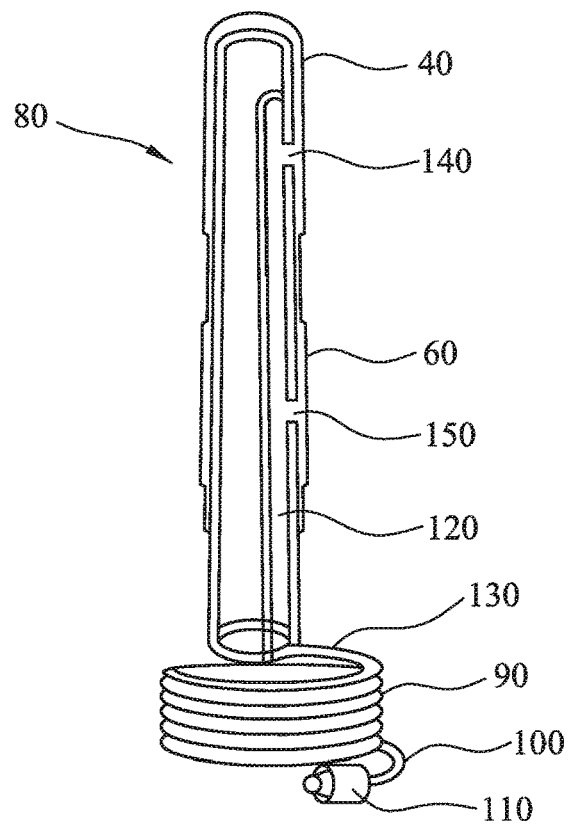
Figure 2

BALLOON FOR CERVICAL RIPENING

FIELD OF INVENTION

The present invention relates to a method, apparatus, and system for cervical ripening to induce labor.

BACKGROUND OF THE INVENTION

Cervical ripening is the process of softening and opening the cervix before labor. Although it may occur naturally, it is sometimes induced. A known method for inducing cervical ripening involves the use of double or single-balloon catheters. In either case, a balloon is inserted intravaginally beyond the cervix and inflated, such as to apply pressure to the cervix. In the case of a double balloon catheter, a second balloon or the vaginal balloon is inflated on the other side of the cervix such as to secure the positioning of the device.

For inflation, fluid is delivered to the balloon(s) via a tube. Once the balloons are inflated, the tube is left hanging out of the vagina and is usually taped to the leg of the patient. The catheter is then left in for 12 to 24 hours before the balloons are deflated by removing fluid via the tube and it is removed.

FIG. 1 shows a known double balloon catheter 10 in use by a patient 20 for ripening the cervix 30. The catheter 10 comprises a first inflatable portion 40. The first inflatable portion 40 is configurable between a deflated and an inflated state. In the deflated state, the first inflatable portion 40 is configured to be inserted into the vagina 50. In this example, the first inflatable portion 40 is a uterine balloon. The uterine balloon 40 is configured to be inserted beyond the cervix 30. The uterine balloon 40 is then inflatable by a fluid. In this example, the fluid is a saline solution. When in the inflated state, the first inflatable portion 40 applies pressure to the cervix 30.

The catheter 10 further comprises a second inflatable portion 60. The second inflatable portion, 60 is configurable between a deflated and an inflated state. In the deflated state, the second inflatable portion 60 is configured to be inserted into the vagina 50. In this example, the second inflatable portion 60 is a vaginal balloon. The vaginal balloon 60 is configured to be inserted shy of the cervix 30. The vaginal balloon 60 is then inflatable by a fluid. In this example, the fluid is a saline solution. When in the inflated state, the second inflatable portion 60 secures the positioning of the catheter 10 within the body of the patient 20.

The catheter 10 further comprises a tube 70. The tube 70 is configured to deliver fluid to the first and the second inflatable portions 40, 60. Once the first and second inflatable portions 40, 60 have been inflated, the tube 70, at least in part, is located outside of the vagina 50. Said hanging portion of the tube 70 is then taped to the leg of the patient 20.

SUMMARY OF THE INVENTION

The invention is defined in the independent claims below, to which reference should now be made. Optional features are set forth in the dependent claims.

An example arrangement is described in more detail below and takes the form of an intravaginal device for cervical ripening comprising an inflatable portion and a tube in fluid communication with the inflatable portion. The inflatable portion is configurable between a deflated and an inflated state, and the inflatable portion is configured to be inserted into a vagina when in the deflated state and to ripen a cervix when inflated with fluid. The tube, or filling tube, is configurable between an extended state and a retracted state. In the extended state, the tube is configured to be located at least in part outside the vagina to deliver fluid to inflate the inflatable portion. In the retracted state, the tube is configured to be located within the vagina. In one example, in the retracted state, the tube has a helical shape configured to be located within the vagina. A helical shape is defined as a shape that is coiled or spring-like.

The inventor has appreciated that the tube of the hanging portion of the tube of known catheter devices can lead to pulling. This causes discomfort for the patient in the lead-up to labor. Furthermore, the inventors have appreciated that the hanging portion being taped to the leg of the patient restricts mobility. The present invention acknowledges and aims to address this problem whilst also acknowledging that access to the tube is required even after insertion for the eventual deflation and removal of the catheter device.

According to one aspect of the present invention, there is provided an intravaginal device for cervical ripening, the intravaginal device comprising: an inflatable portion configurable between a deflated and an inflated state. The inflatable portion is configured to be inserted into a vagina when in the deflated state and to ripen a cervix when inflated with fluid, and a tube in fluid communication with the inflatable portion, the tube being configurable between an extended state and a retracted state, wherein in the extended state the tube is configured to be located at least in part outside the vagina to deliver fluid to inflate the inflatable portion and wherein in the retracted state the tube is configured to be located within the vagina.

In one example, in the retracted state, the tube has a helical shape.

In one example, the inflatable portion is a uterine balloon configured to be located beyond the cervix for ripening the cervix when in the inflated state.

In one example, the intravaginal device further comprises a second inflatable portion configurable between a deflated and an inflated state, the second inflatable portion configured to be inserted into the vagina when in the deflated state.

In one example, the second inflatable portion is a vaginal balloon configured to be located within the vagina, such as to secure the location of the first inflatable portion when the second inflatable portion is in the inflated state.

In one example, the intravaginal device further comprises a channel in fluid communication with a distal end of the tube, the channel being configured to deliver fluid from the tube to the first inflatable portion and the second inflatable portion.

In one example, the channel comprises a first aperture enclosed within the inflatable portion, the first aperture being configured to deliver fluid from the channel to the inflatable portion.

In one example, the channel comprises a second aperture enclosed within the second inflatable portion, the second aperture being configured to deliver fluid from the channel to the second inflatable portion.

In one example, when in the retracted state, the tube is configured to be located entirely within the vagina.

In one example, the fluid is a saline solution.

The inventor has appreciated that the known intravaginal devices can be difficult to insert. The present invention acknowledges and aims to improve the ease of insertion of an intravaginal device.

According to another aspect of the present invention, there is provided an insertion device for insertion of an intravaginal device for cervical ripening, the insertion device comprising: an elongate member having a distal portion configured to engage with and insert an intravaginal device for ripening a cervix; and the elongate member comprising a light source, the light source being configured to provide a source of light for illuminating an area of insertion of the intravaginal device.

In one example, the light source is a light-emitting diode.

In one example, the insertion device further comprises a battery.

According to another aspect of the present invention there is provided a system for inserting and inflating an intravaginal device, the system comprising: an intravaginal device comprising an inflatable portion configurable between a deflated and an inflated state, the inflatable portion configured to be inserted into a vagina when in the deflated state and to ripen a cervix when inflated with fluid, and a tube in fluid communication with the inflatable portion, the tube being configurable between a extended state and a retracted state, wherein in the extended state the tube is configured to be located at least in part outside the vagina to deliver fluid to inflate the inflatable portion and wherein in the retracted state the tube is configured to be located within the vagina; and an insertion device comprising an elongate member having a distal portion configured to engage with and insert the intravaginal device, and the elongate member comprising a light source, the light source being configured to provide a source of light for illuminating an area of insertion.

In one example, in the retracted state, the tube has a helical shape.

In one example, the elongate member comprises a curved portion configured to removably reside within the helical shape of the tube.

In one example, the system further comprises a valve coupled to a proximal end of the tube.

In one example, the elongate member further comprises a mechanism configured to retain the valve when the tube is in the extended state.

In one example, the distal portion of the elongate member is configured to removably engage with the inflatable portion.

According to another aspect of the present invention, there is provided a method of inflating an intravaginal device for cervical ripening. The method comprising: inserting an inflatable portion configurable between a deflated and an inflated state into a vagina when in the deflated state, the inflatable portion being inflatable with fluid to ripen a cervix; delivering fluid to inflate the inflatable portion via a tube in fluid communication with the inflatable portion, the tube being in an extended state such that it is located at least in part outside the vagina; and retracting the tube into a retracted state in which it is located within the vagina.

According to another aspect of the present invention, there is provided a method of inserting and inflating an intravaginal device for cervical ripening, the method comprising: engaging a distal portion of an elongate member of an insertion device with an intravaginal device; illuminating an area of insertion using a light source of the elongate member; inserting an inflatable portion of the intravaginal device configurable between a deflated and inflated state into a vagina when in the deflated state via the distal portion of the elongate member, the inflatable portion being inflatable with fluid to ripen a cervix; delivering fluid to inflate the inflatable portion via a tube in fluid communication with the inflatable portion, the tube being in an extended state such that it is located at least in part outside the vagina; and retracting the tube into a retracted state in which it is located within the vagina.

BRIEF DESCRIPTION OF THE DRAWINGS

The invention will be described in more detail by way of example with reference to the accompanying drawings, in which:

FIG. 1 (prior art) is a schematic diagram of a known double balloon catheter;

FIG. 2 is a schematic diagram of an intravaginal device according to aspects of the present disclosure;

DETAILED DESCRIPTION

Figure 3:
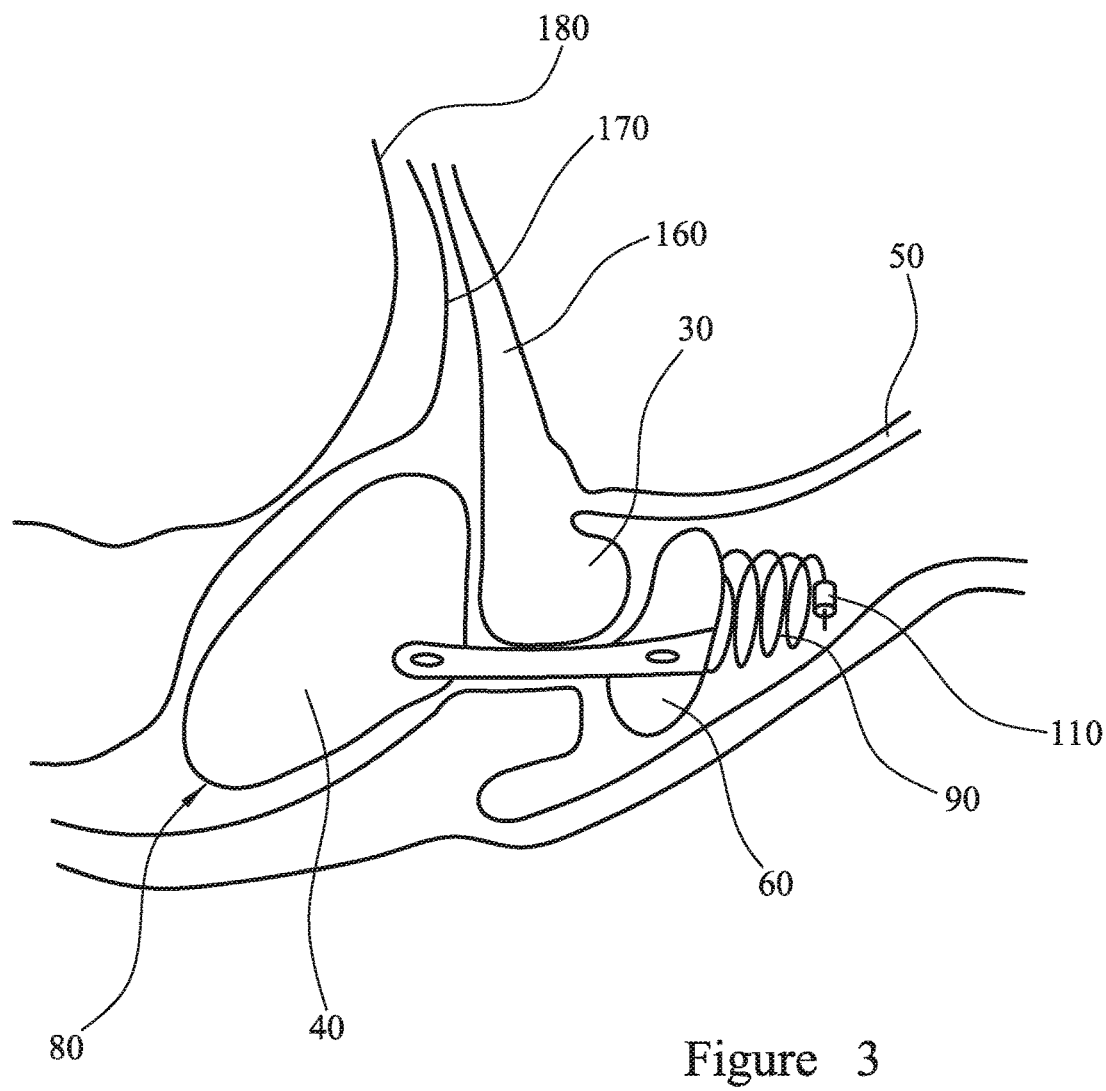
FIG. 3 is a schematic diagram of the intravaginal device of FIG. 2 inflated for use according to aspects of the present disclosure.

An example intravaginal device 80, according to aspects of the present invention, is shown in FIGS. 2 and 3. The device shares like features with the known double balloon catheter 10 of FIG. 1, and like features have been given like reference numerals. The configuration of the tube 90, however, is significant and is discussed in more detail below.

FIG. 2 shows an example intravaginal device 80 in which the first inflatable portion 40 and the second inflatable portion 60 are in the deflated state. The intravaginal device 80 comprises a tube 90. The tube 90 is in fluid communication with the first and second inflatable portions 40, 60. Once the first and second inflatable portions 40, 60 have been positioned on either side of the cervix when in the deflated state, the tube 90 is used to deliver fluid to inflate them. The tube 90 is configurable between an extended state and a retracted state. In the retracted state, the tube 90 has a helical or spiral shape. In this example, the retracted state is the state the tube 90 has when it is not being stretched. In the extended state, the helical or spiral shape of the tube 90 is elongated. To inflate the first and second inflatable portions 40, 60, the tube 90 is stretched into the extended state by a user. In this example, the user is the one inserting the intravaginal device 80 on behalf of the patient. In practice, the user is likely to be a physician. In this way, the tube 90 is, at least in part, located outside of the vagina. A proximal end 100 of the tube 90 is, therefore, accessible by the user. Fluid is then delivered to the first and second inflatable portions 40, 60 via a valve 110 at said proximal end 100. Once the first and second inflatable portions 40, 60 are in the inflated state, the tube 90 is released by the user. The tube 90, therefore, assumes its retracted state. The helical shape of the tube 90 in the retracted state is configured to be located within the vagina. In this example, the helical shape of the tube 90 is configured to be located entirely within the vagina when in the retracted state. Therefore, once inserted and the inflatable portions 40, 60 inflated, the device 80 is completely intravaginal. In this way, the tube 90 can be considered spring like or elastic. After insertion and filling of the balloons 40, 60 by a physician, the tube 90 springs back to its pre-elongation shape and size to be placed wholly intravaginal. To subsequently deflate the first and second inflatable portions 40, 60 and remove the device, the tube can be extended again such that the valve is accessible outside of the vagina. The fluid can then be removed from the inflatable portions 40, 60 via the tube 90.

The tube 90 delivers fluid to the first and second inflatable portions 40, 60 via a channel 120. The channel 120 extends through the intravaginal device 80. In this example, the channel 120 is in fluid communication with a distal end 130 of the tube 90. The channel 120 further comprises first and second apertures 140, 150. The first aperture 140 is enclosed by the first inflatable portion 40. The second aperture 150 is enclosed by the second inflatable portion 60. The first and second apertures 140, 150 are, therefore, configured to deliver fluid from the channel 120, respectively to the first and second inflatable portions 40, 60. The first and second inflatable portions 40, 60 are configured to be of fixed volume when in the inflated state. They are further configured to be of fixed shape when in the inflated state. This is enabled by the material of the first and second inflatable portions 40, 60. The shape and volume are such that the balloons 40, 60 are effective with least inflation.

FIG. 3 shows the intravaginal device 80 of FIG. 2, the device 80 having been inserted into the vagina 50 and the first and second inflatable portions 40, 60 being in the inflated state. The first inflatable portion 40 is located beyond the cervix 30, in the lower part of the uterus 160 and adjacent to the amnion 170 and the head of the baby 180. The second inflatable portion 60 is located within the vagina 50. The tube 90 is in the retracted state. It is, therefore, wholly intravaginal. This is advantageous over the known device of FIG. 1 as the tube 90 is not left to hang outside of the patient's body, leaving the tube prone to pulling and causing discomfort for the patient. The device 80, according to aspects of the present disclosure, therefore, causes less discomfort to the patient while waiting for labor to begin.

Figure 4:
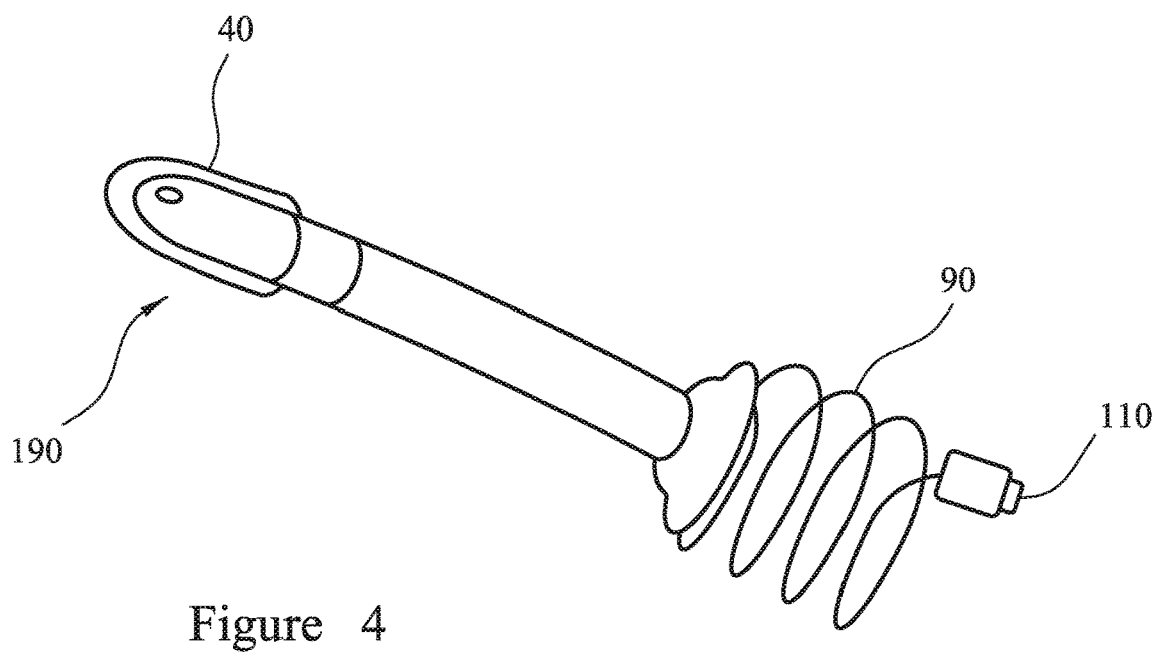
FIG. 4 is a schematic diagram of a second embodiment of an intravaginal device according to aspects of the present disclosure.
Figure 5:
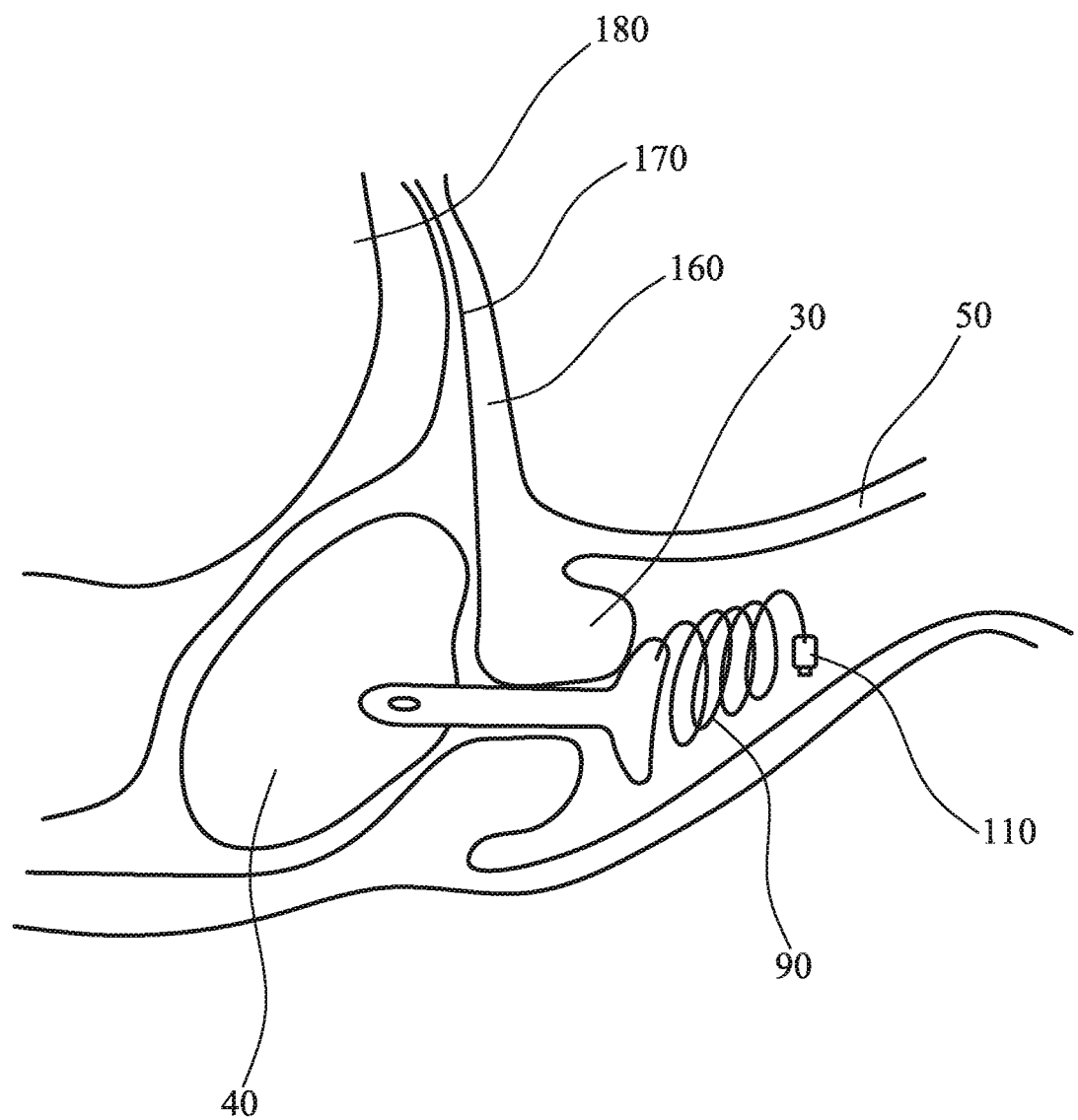
FIG. 5 is a schematic diagram of the intravaginal device of FIG. 4 inflated for use according to aspects of the present disclosure.

A second embodiment of an intravaginal device 190 according to aspects of the present invention is shown in FIGS. 4 and 5. The device shares like features with the intravaginal device 80 of FIGS. 2 and 3 and like features have been given like reference numerals. In the second embodiment, however, the intravaginal device 190 only comprises a single inflatable portion 40 corresponding to the first inflatable portion 40 of the device 80 shown in FIGS. 2 and 3. The intravaginal device 190, therefore, only comprises a uterine balloon 40 and not a vaginal balloon. FIG. 4 depicts the device 190 with the inflatable portion 40 in the deflated state. FIG. 5 depicts the device 190 once it has been inserted for use and the inflatable portion 40 is in the inflated state.

According to another aspect of the present invention, with reference to FIGS. 6 to 9 described below, there is provided an insertion device for the insertion of the intravaginal devices of FIGS. 2 to 5 described above.

Figure 6:
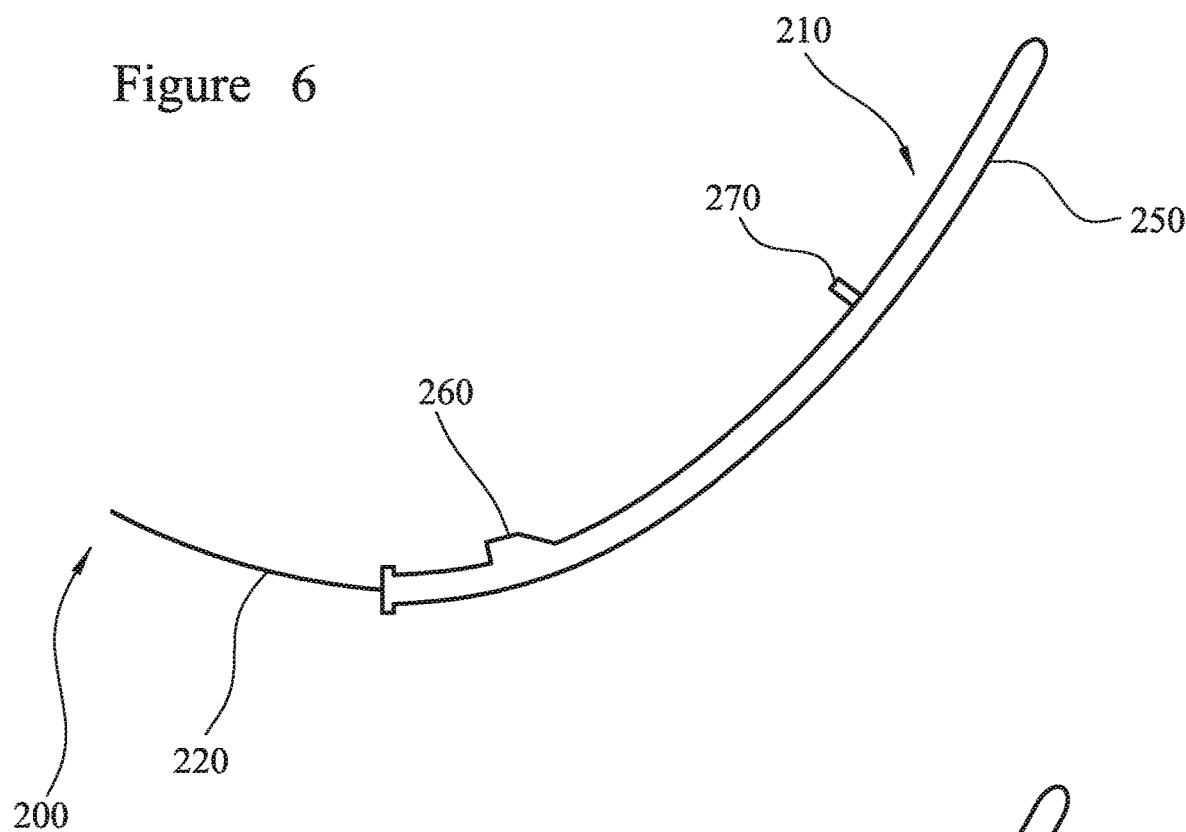
FIG. 6 is a schematic diagram of an insertion device according to aspects of the present disclosure.

An example insertion device 200 is shown in FIG. 6. The insertion device 200 comprises an elongate member 210. The elongate member 210 is between 20 centimeters and 40 centimeters in length. Specifically, in this example, the elongate member 210 is 30 centimeters in length. The elongate member 210 is curved in shape. The elongate member 210 has a distal portion 220 configured to engage with and insert an intravaginal device. The distal portion 220 is formed of between the distal 3 centimeters and 10 centimeters of the elongate member 210. Specifically, in this example, the distal portion 220 is formed of the distal 5 centimeters of the elongate member 210.

Figure 7:
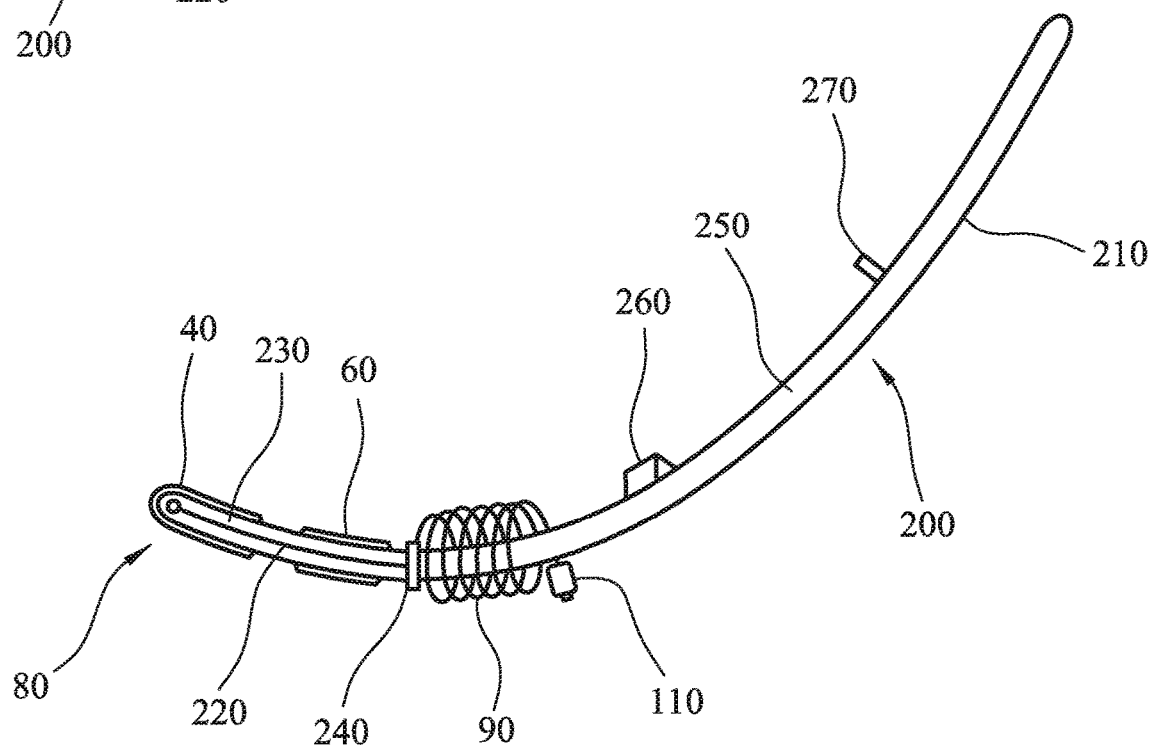
FIG. 7 is a schematic diagram of the intravaginal device of FIG. 2 and the insertion device of FIG. 6.
Figure 8:
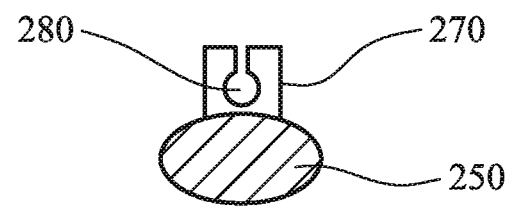
FIG. 8 is a schematic diagram of a clip of the insertion device of FIG. 6.

FIG. 7 shows the distal portion 220 of the insertion device 200 engaged with the intravaginal device 80 of FIGS. 2 and 3. The distal portion 220 engages with a cavity 230 of the intravaginal device 80. The cavity 230 comprises an opening 240 at its proximal end. The cavity 230 extends through the first inflatable portion 40 and the second inflatable portion 60. The cavity 230 further extends alongside the channel of the intravaginal device 80. In this way, the first and second inflatable portions 40, 60 are configured to inflate around the cavity 230. The diameter of the cavity 230 is between two and ten times that of the distal portion 220 of the insertion device 200. Specifically, in this example, the diameter of the cavity 230 is five times that of the distal portion 220 of the insertion device 200. The length of the distal portion 220 is comparable to that of the cavity 230.

The elongate member 210 further comprises a handle portion 250 for the purpose of guiding insertion. The handle portion 250 has a diameter comparable to that of the cavity 230. When the distal portion 220 of the insertion device 200 is engaged with the cavity 230, the handle portion 250 is configured to be located within the helical structure of the tube 90 of the intravaginal device 80.

The elongate member 210 further comprises a light source 260. This feature is significant. The light source 260 is configured to provide a source of light for illuminating the area of insertion of the intravaginal device 80. In this example, the light source 260 is a light-emitting diode (LED). The light source 260 is integrated with the elongate member 210. In this example, the light source 260 protrudes from the handle portion 250. The light source 260 is configured such that its light is directed towards the distal portion 220 of the insertion device 200. In this way, the light source 260 is configured to illuminate the intravaginal device 80 itself and the area of insertion. This aids insertion. The insertion device 200 further comprises a battery (not shown) inside the elongate member to power the light source 260. A switch (not shown) is also provided on the elongate member 201 for a user to turn the light source on and off.

The elongate member 210 further comprises an arrangement or mechanism 270 for retaining the valve 110 of the intravaginal device 80. In this example, the arrangement 270 is a clip, shown in more detail in FIG. 8. The clip 270 protrudes from the handle portion 250. The clip 270 further comprises a slit 280 into which the valve 110 of the intravaginal device 80 can be pushed for retention. The clip 270 is positioned such that it is configured to retain the valve 110 when the intravaginal device 80 is engaged with the insertion device 200, and the tube 90 is in its extended state. The clip 270 is, therefore, nearer the proximal end than the distal end of the insertion device 200.

Figure 9:
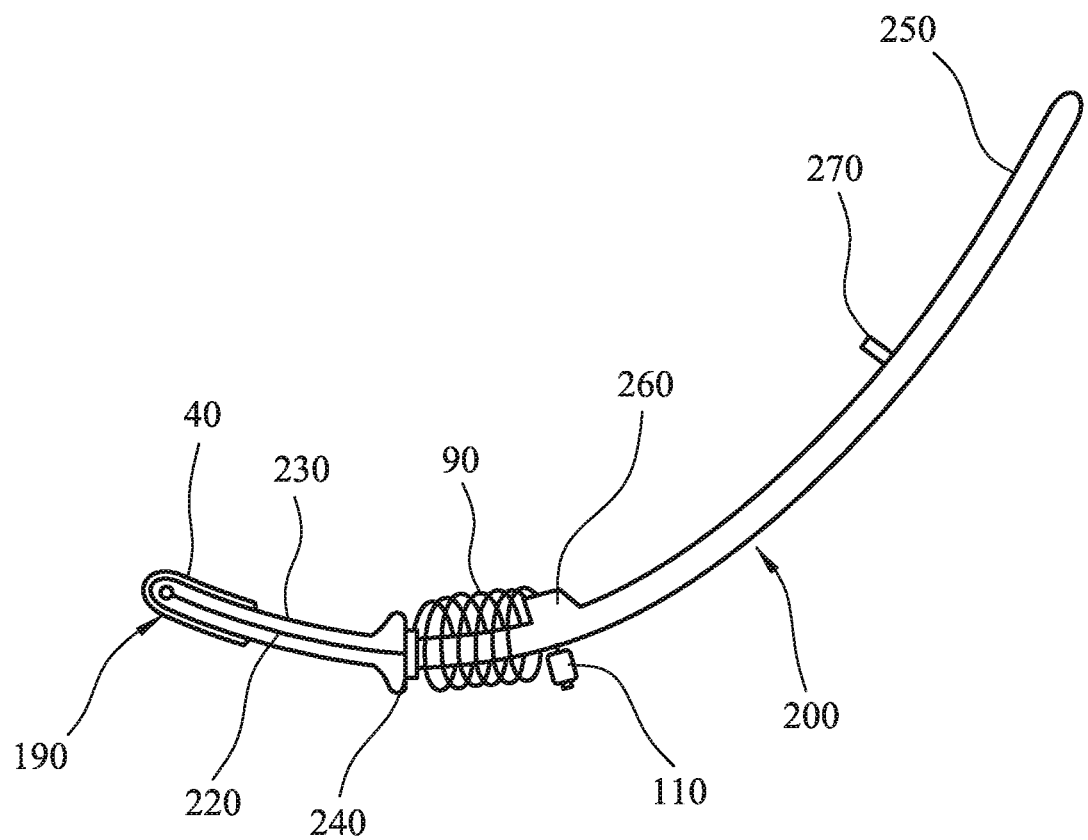
FIG. 9 is a schematic diagram of the intravaginal device of FIG. 4 and the insertion device of FIG. 6.

FIG. 9 shows the distal portion 220 of the insertion device 200 engaged with the intravaginal device 190 of FIGS. 4 and 5. Again, like features have been given like reference numerals.

Referring to FIGS. 7 and 9, to insert and subsequently inflate the intravaginal device 80, 190, the user engages the distal portion 220 of the insertion device 200 with the cavity 230 of the intravaginal device 80, 190 via its opening 240. The user then extends the tube 90 of the intravaginal device 80, 190 such that it assumes its extended state and pushes the valve 110 at the proximal end of the tube 90 into the clip 270 of the insertion device 200. Using the handle portion 250 of the insertion device 200, the intravaginal device 80, 190 is inserted into the vagina such that the uterine balloon 40 is located beyond the cervix and the vaginal balloon 60, if included, is located within the vagina. This process is aided by illuminating the area of insertion using the light source 260 such that visualization of the uterine cervix is improved. Fluid is then delivered to inflate the balloons 40, 60 via the valve 110, which is accessible outside of the vagina due to the tube 90 being held in the extended state by the clip 270. Once inflated, the valve 110 is removed from the clip 270. The tube 90, as a result, retracts such that it is wholly intravaginal. The distal portion 220 of the insertion device 200 is then removable using the handle portion 250. Removing the distal portion 220 from the cavity 230 of the intravaginal device 80, 190 does not, in turn remove the intravaginal device 80, 190 as the inflated balloons 40, 60 hold the device in place.

Embodiments of the present invention have been described with particular reference to the examples illustrated. However, it will be appreciated that variations and modifications may be made to the examples described within the scope of the present invention.

I claim:

1. An intravaginal device for cervical ripening and for use with an insertion device, the intravaginal device comprising:
    a shaft having a distal end and a proximal end, the shaft having a channel to allow positioning of the shaft over the insertion device, where the distal end is closed to prevent passing of the insertion device beyond the distal end of the shaft;
    a first inflatable portion configurable between a deflated state and an inflated state, the first inflatable portion configured to be inserted into a vagina when in the deflated state and to ripen a cervix when inflated with fluid, the first inflatable portion located at the distal end of the shaft;
    a second inflatable portion configurable between a deflated state and an inflated state, the second inflatable portion configured to be inserted into the vagina when in the deflated state and wherein the second inflatable portion is a vaginal balloon configured to be located within the vagina shy of the cervix such as to secure a location of the first inflatable portion when the second inflatable portion is in the inflated state, the second inflatable portion located at the proximal end of the shaft, such that when the second inflatable portion is located within the vagina, a portion of the shaft is within the cervix; and
    a tube extending from the proximal end of the shaft, the tube in fluid communication with the first inflatable portion and the second inflatable portion through the channel, the tube being configurable between an extended state and a retracted state, wherein in the extended state the tube is configured to be located at least in part outside the vagina to deliver fluid to inflate the first inflatable portion and the second inflatable portion, and wherein in the retracted state the tube is configured to be located within the vagina.

2. The intravaginal device of claim 1 wherein in the retracted state, the tube has a helical shape.

3. The intravaginal device of claim 1 wherein the first inflatable portion is a uterine balloon configured to be located beyond the cervix for ripening the cervix when in the inflated state.

4. The intravaginal device of claim 1 wherein the channel comprises a first aperture enclosed within the first inflatable portion, the first aperture being configured to deliver fluid from the channel to the first inflatable portion.

5. The intravaginal device of claim 1 wherein the channel comprises a second aperture enclosed within the second inflatable portion, the second aperture being configured to deliver fluid from the channel to the second inflatable portion.

6. The intravaginal device of claim 1 wherein when in the retracted state the tube is configured to be located entirely within the vagina.

7. The intravaginal device of claim 1 wherein the fluid is a saline solution.

8. A system for inserting and inflating an intravaginal device, the system comprising:
    an intravaginal device comprising a shaft having a distal end and a proximal end, a first inflatable portion located at the distal end and configurable between a deflated state and an inflated state, the first inflatable portion configured to be inserted into a vagina when in the deflated state and to ripen a cervix when inflated with fluid, a second inflatable portion located at the proximal end such that when the second inflatable portion is located within the vagina, the shaft remains entirely within the vagina, the second inflatable portion configurable between a deflated and an inflated state, the second inflatable portion configured to be inserted into the vagina when in the deflated state and wherein the second inflatable portion is a vaginal balloon configured to be located within the vagina shy of the cervix such as to secure a location of the first inflatable portion when the second inflatable portion is in the inflated state, and a tube in fluid communication with the first inflatable portion and the second inflatable portion, the tube being configurable between an extended state and a retracted state, wherein in the extended state the tube is configured to be located at least in part outside the vagina to deliver fluid to inflate the first inflatable portion and the second inflatable portion and wherein in the retracted state the tube is configured to be located within the vagina; and
    an insertion device comprising an elongate member having a curved shape, the elongate member having a distal portion configured to engage with and insert the intravaginal device, and the elongate member comprising a light source, the light source being configured to provide a source of light for illuminating an area of insertion and wherein the light source is integrated with the elongate member, where the distal end of the shaft is closed to prevent passing of the insertion device beyond the distal end of the shaft.

9. The system of claim 8 wherein in the retracted state the tube has a helical shape.

10. The system of claim 9 wherein the elongate member comprises a curved portion configured to removably reside within the helical shape of the tube.

11. The system of claim 8 further comprising a valve coupled to a proximal end of the tube.

12. The system of claim 11 wherein the elongate member further comprises a clip mechanism configured to retain the valve when the tube is in the extended state.

13. The system of claim 8 wherein the distal portion of the elongate member is configured to removably engage with the first inflatable portion.

14. An intravaginal system for cervical ripening, the system comprising:
    an insertion device having an elongate shape;
    an intravaginal device comprising:
        a shaft having a distal end and a proximal end, the shaft having a channel to allow positioning of the shaft over the elongate shape of the insertion device, where the distal end is closed to prevent passing of the insertion device beyond the distal end of the shaft;

a first inflatable portion configurable between a deflated state and an inflated state, the first inflatable portion configured to be inserted into a vagina when in the deflated state and to ripen a cervix when inflated with fluid, the first inflatable portion located at the distal end of the shaft;

a second inflatable portion configurable between a deflated state and an inflated state, the second inflatable portion configured to be inserted into the vagina when in the deflated state and wherein the second inflatable portion is a vaginal balloon configured to be located within the vagina shy of the cervix such as to secure a location of the first inflatable portion when the second inflatable portion is in the inflated state, the second inflatable portion located at the proximal end of the shaft, such that when the second inflatable portion is located within the vagina, a portion of the shaft is within the cervix; and a tube extending from the proximal end of the shaft, the tube in fluid communication with the first inflatable portion and the second inflatable portion through the channel, the tube being configurable between an extended state and a retracted state, wherein in the extended state the tube is configured to be located at least in part outside the vagina to deliver fluid to inflate the first inflatable portion and the second inflatable portion, and wherein in the retracted state the tube is configured to be located within the vagina.

15. The intravaginal system of claim 14, wherein:

the insertion device comprises a distal portion having a curved shape and configured to receive the intravaginal device; and wherein the insertion device includes a light source configured to provide illumination of an area of insertion of the intravaginal device and wherein the light source is integrated with the insertion device.

16. The intravaginal system of claim 15, wherein the light source is a light emitting diode.

17. The intravaginal system of claim 15, further comprising a battery electrically coupled to the light source.

\* \* \* \* \*